(12) United States Patent
Rezania et al.

(10) Patent No.: US 8,017,395 B2
(45) Date of Patent: Sep. 13, 2011

(54) SEEDING CELLS ON POROUS SUPPORTS

(75) Inventors: Alireza Rezania, Hillsborough, NJ (US);
Ragae Ghabrial, Helmetta, NJ (US)

(73) Assignee: Lifescan, Inc., Milpitas, CA (US)

( * ) Notice: Subject to any disclaimer, the term of this patent is extended or adjusted under 35 U.S.C. 154(b) by 678 days.

(21) Appl. No.: 11/303,244

(22) Filed: Dec. 16, 2005

(65) Prior Publication Data

US 2006/0177924 A1      Aug. 10, 2006

Related U.S. Application Data

(60) Provisional application No. 60/637,401, filed on Dec. 17, 2004.

(51) Int. Cl.
*C12N 5/02* (2006.01)

(52) U.S. Cl. ..................................... 435/399; 435/297.1

(58) Field of Classification Search .......................... None
See application file for complete search history.

(56) References Cited

U.S. PATENT DOCUMENTS

| | | | |
|---|---|---|---|
| 3,935,067 A | 1/1976 | Thayer | |
| 4,557,264 A | 12/1985 | Hinsch | |
| 5,686,090 A | 11/1997 | Schilder | |
| 5,713,957 A * | 2/1998 | Steele et al. | 623/5.16 |
| 7,390,484 B2 * | 6/2008 | Fraser et al. | 424/93.7 |
| 2004/0062753 A1 | 4/2004 | Rezania | |

FOREIGN PATENT DOCUMENTS

| | | |
|---|---|---|
| CA | 134 1061 | 7/2000 |
| EP | 0423155 B1 | 4/1991 |
| EP | 0325195 B1 | 8/1993 |
| EP | 0878205 A2 | 11/1998 |

OTHER PUBLICATIONS

Martin et al., "Bioreactors for tissue mass culture: Design, characterization, and recent advances", Biomaterials, Elsevier Science Publishers BV, Barking, GB, vol. 26, No. 35, Dec. 2005.

Takahashi, Yoshitake et al., "Homogeneous seeding of mesenchymal stem cells into nonwoven fabric for tissue engineering", Tissue Engineering, vol. 9, No. 5, Oct. 2003, pp. 931-938.

Tsung, Hua Yang et al., "Novel cell immobilization method utilizing centrifugal force to achieve high-density hepatocyte culture in porous scaffold", Journal of Biomedical Materials Research, Jun. 2001, vol. 55, No. 3, pp. 379-386.

Van Wachem, P.B. et a., "Vacuum cell seeding a new method for the fast application of an evenly distributed cell layer on porous vascular grafts", Biomaterials, vol. 11, No. 8, 1990, pp. 602-606.

Young, Roger C. et al., "Three-dimensional culture of human uterine smooth muscle myocytes on a resorbable scaffolding", Tissue Engineering, vol. 9, No. 3, Jun. 2003, pp. 451-459.

Dar, et al., "Cardiac Tissue Engineering: Optimization of Cardiac Cell Seeding and Distribution in 3D Porous Alginate Scaffolds", Biotechnol. Bioeng., vol. 80 No. 3, pp. 305-312, (2002).

Vunjak-Novakovic, et al., "Dynamic Cell Seeding of Polymer Scaffolds for Cartilage Tissue Engineering", Biotechnol. Prog. vol. 14 No. 2, pp. 193-202, (1998).

Yang, et al., "Novel Cell Immobilization Method Utilizing Centrifugal Force to Achieve High-Density Hepatocyte Culture in Porous Scaffold", Journal of Biomedical Mater. Res. vol. 55, No. 3, pp. 379-386, (2001).

* cited by examiner

*Primary Examiner* — James S Ketter
(74) *Attorney, Agent, or Firm* — Mark R. Warfield

(57) ABSTRACT

The present invention generally relates to a method for seeding cells on to a support. In particular, the method relates to a method for seeding cells onto a porous hydrophobic support. The method utilizes centrifugal forces to uniformly guide cell seeding into the support with no loss in viability.

1 Claim, 3 Drawing Sheets

SEEDING CELLS ON POROUS SUPPORTS

CROSS REFERENCE TO RELATED APPLICATIONS

This application claims the benefit of U.S. Provisional Application No. 60/637,401, filed on Dec. 17, 2004, which is incorporated by reference herein in its entirety.

FIELD OF THE INVENTION

The present invention relates to a method for seeding cells onto a support.

BACKGROUND OF THE INVENTION

Transplantation of tissue into an animal, such as, for example, stem cells, cells cultured in vitro, or isolated primary cells, typically involves direct introduction of cellular material into the recipient, either into the blood stream or directly into a tissue. However, these procedures are associated with significant complications, such as thrombosis, which reduces cell survival.

Tissue engineering can provide a solution to this problem by providing a three dimensional support that acts as a substrate for cell attachment. It has been previously demonstrated that cells seeded in a properly designed support could recreate the in-vivo microenvironment, thereby facilitating cell-cell interactions and expression of differentiated functions. To construct such complex structures, the efficiency of the cell seeding process can be important to the overall performance of the tissue-engineered construct.

Prior to the present invention, seeding of cells onto supports has involved simple depositing of cells onto the support by relying on passive diffusion of cells into the support. Several other approaches have been developed to enhance the efficiency of cell seeding. For example, spinner flasks have been used in seeding of chondrocytes onto polyglycolic acid supports (Vunjak-Novakovic et al., "Dynamic cell seeding of polymer supports for cartilage tissue engineering," *Biotechnol. Prog.* 14(2):193-202, 1998). The procedure involved suspending the supports via needles in a cell suspension and mixing with a magnetic stir bar at 50 rpm. The process required a long time to complete, ranging from several hours to one day.

Another approach for seeding cells is the use of centrifugation, which yields minimum stress to the seeded cells and enhances seeding efficiency. A cell seeding method was developed by Yang et al. (*J. Biomed. Mater. Res.* 55(3): 379-86, 2001), referred to as Centrifugational Cell Immobilization (CCI). Hepatocytes were seeded onto hydrophilic porous poly (vinyl formal) cubes. Both the cubes and hepatocytes were suspended in media in a centrifugation tube and were exposed to alternating centrifugation and resuspension steps. The procedure yielded 40% seeding efficiency and required a large number of hepatocytes (2-8×10$^7$ cells). Dar et al. (*Biotechnol. Bioeng.* 80(3): 305-12, 2002) utilized a more controlled approach in cell seeding via centrifugation. Cardiomyocytes were seeded onto a hydrophilic alginate support by placing the support into a well of a 96-well plate and pipetting 10 µl of cell suspension onto it. The plate was then placed onto a plate holder-type rotor and centrifuged for 6 minutes at 1000×g, 4° C. A seeding efficiency of 80-90% was reported in an alginate support, which decreased to 60% when higher seeding densities were used per support. The centrifugation methods described above have yielded some success but have limitations. A vital issue in the process is the porosity of the support. The centrifugal force pressures the cell suspension through the support where the cellular material gets entangled within the pores of the support. If the porosity is too large, the cellular material passes all the way through the support to the bottom of the centrifugation chamber leading to a drop in seeding efficiency. On the other hand, lowering the porosity of the support to accommodate this issue may have a negative effect on the survival of the seeded cellular material. A high porosity is essential in allowing diffusion of oxygen and nutrition.

Seeding cells onto a hydrophobic support is usually more complex than onto a hydrophilic one. Cells are usually suspended in a culture media solution with water being the major component. A hydrophobic support repels a cell suspension preventing cells from infiltrating said support. In order to overcome such barrier, a driving force is required. The force regardless of its source exposes the cells to a stress component that is harmful to the cells. Thus, there remains a need to develop a simple and reproducible method to seed cells onto porous supports particularly hydrophobic ones with high seeding efficiency and little or no loss in cell viability.

SUMMARY

The present invention provides a method for seeding cells of any type onto a support. The process of the current invention may be designed not to expose the seeded cells to any forces that might affect cell viability or function. The method may exert no harmful forces on the cells to uniformly guide cell seeding into the support, achieving high seeding efficiency and no significant loss in cell viability. The method of the present invention may also be more efficient in reducing contamination issues. Using a force to facilitate the seeding of cells onto a support may involve further processing of the cells, which in turn increases contamination chances.

The present invention also provides a kit for seeding cells onto a biocompatible support.

DETAILED DESCRIPTION

Figure 1:
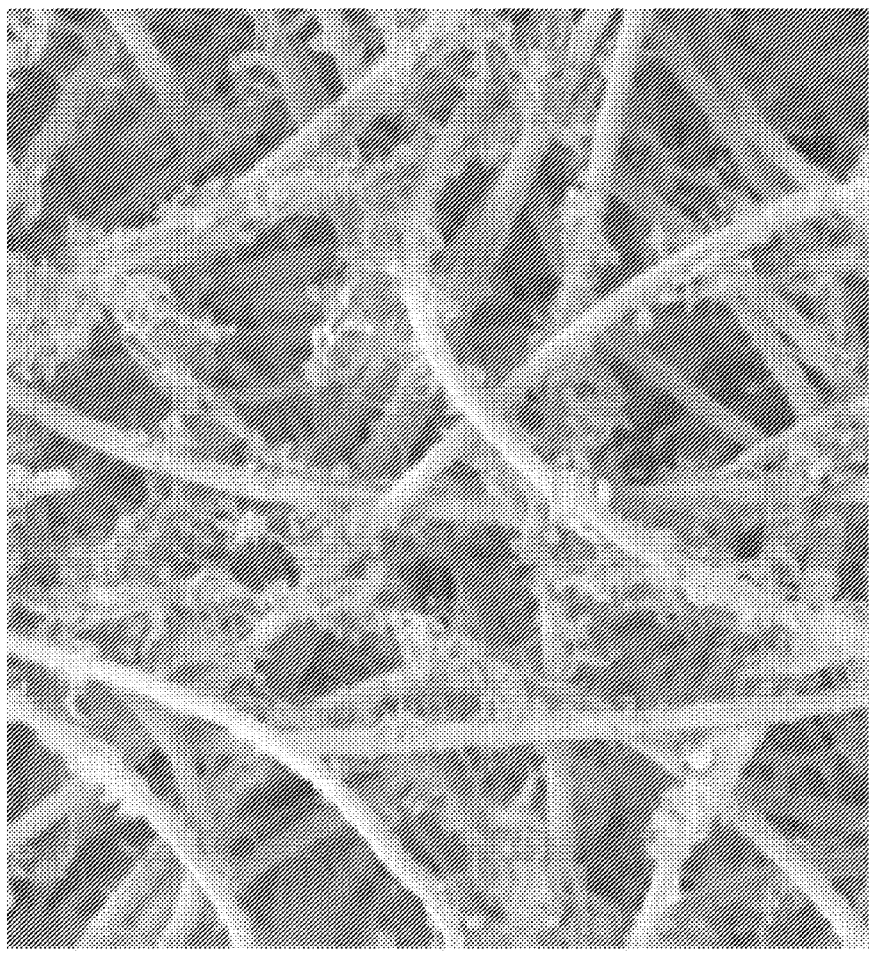
FIG. 1: Electron micrograph of a nonwoven support of the present invention. The matrix of the support is composed of fibers made from VICRYL®.

The term "support" as used herein refers to a three-dimensional architecture that is capable of supporting cells on the surface or within the architecture.

The term "porous" as used herein refers to a plurality of openings in the support that may or may not lead to interconnecting, interstitial spaces within the support that enables the uniform distribution of nutrients and cells within the support.

The term "biocompatible" refers to the ability of the support to reside within a mammal so as not to induce toxic or undesirable effects in that mammal.

By "biodegradable" or "absorbable" is meant that the device may be gradually degraded or absorbed by natural biological processes after the device is delivered to a site of interest within a mammal.

The term "matrix" as used herein refers to the material that comprises the solid component of a support.

The term "hydrophobic support," as used herein, refers to a support comprised of a polymer that doesn't wet readily when in contact with water. For example, one with a contact angle with water above 10°, more specifically one with a contact angle above 45° would be considered to be hydrophobic.

The term "hydrophilic support," as used herein, refers to a support comprised of a polymer that does wet readily when in contact with water. For example, one with a contact angle with water below 45°, and more specifically one with a contact angle below 10°, would be considered to be hydrophilic.

The seeding method of the present invention can be applied to any cell type. The term "cells," as used herein, refers to isolated cells, cell lines (including cells engineered in vitro), any preparation of living tissue, including primary tissue explants and preparations thereof.

The term "media," as used herein, refers to a liquid that is used to hydrate the supports of the present invention. The media is non-toxic to cells and is compatible with the liquid that is used to introduce cellular material to the support.

The term "culture media," as used herein, refers to a liquid that is used to introduce cells into the supports of the present invention. The culture media may or may not be that which is used to propagate the cells in vitro. The culture media is non-toxic to cells and is compatible with the liquid that is employed to hydrate the supports of the present invention.

Seeding Cells Onto Supports

The process of the current invention may be specifically designed not to expose the seeded cells to any forces that might affect cell viability or function. In general, a support is brought into contact with liquid, and the liquid flows into support's inner pores until they are completely, or nearly completely, filled with liquid. In one aspect of the invention, the liquid is media. The degree to which the support is filled will depend on the type of support and the amount and type of cells to be entrained therein. Force is then applied to remove a desired amount of liquid to create sufficient volume, or voids, in the support for the subsequent introduction of cellular material.

For example, the support may then be placed on a filter in a centrifugation chamber and centrifuged to remove some, but not all, of the liquid that has been introduced therein. The support is then removed from the filter and placed in a cell culture plate. A certain volume of liquid loaded with cells is then used to refill the potential volume or partial voids that were created via centrifugation. In one aspect of the invention, the liquid is culture media. Since the support is not completely dry, it readily accepts the liquid allowing the cells into the support without any cell loss or any exposure to external forces.

While centrifugation is one method of applying force to remove liquid, other types of force may be used to accomplish the same effect. For example, it is easily conceivable that the application of a compressive force or the application of a vacuum may also be used to remove the desired amount of liquid. It is also possible, for a support that has interconnected interstitial spaces, for a syringe to be used to remove the desired amount of liquid. Such supports could be, for example, those disclosed in US20040062753 A1 and U.S. Pat. No. 4,557,264.

The amount of force to be used to remove liquid that has been introduced into the support may be controllable to allow for the removal of the desired amount of liquid. In the case of a centrifuge, the time and rotational speed of the centrifuge can be varied through normal experimentation to achieve such removal. In the case where compressive force or vacuum is employed, such removal can, again, be obtained through normal experimentation. In one embodiment, the amount of liquid that is removed should equal or exceed the volume of cellular material that is to be subsequently introduced into the support.

By employing the method of the present invention, cell seeding onto a porous support is achieved with a high seeding efficiency without significant loss of cell viability. Seeding efficiency is considered to be high if it is more than about 10%, alternatively more than about 20%, alternatively more than about 30%, alternatively more than about 40%, alternatively more than about 50%, alternatively more than about 60%, alternatively more than about 70%, alternatively more than about 80%, alternatively more than about 90%. Loss of viability of more than about 70% is considered to be significant. In one embodiment, the loss of viability is less than about 10%, alternatively, the loss of viability is less than about 5%.

In one aspect of the present invention, supports may be placed in culture media until the support becomes fully infiltrated with liquid and no air spaces remain in the pores. The soaked supports may then placed on a filtration chamber that fits onto a plate, container or device that in turn fits onto a rotor in a centrifugation chamber. Centrifugation forces may then used to remove a portion of the culture media in the support, creating empty spaces and/or flexibly and reversibly collapsing the matrix of the support within the pores or interstitial space of the support. Cells may then be introduced into the support by first suspending the cells in a volume of culture media that is equal or less to the volume of culture media that is displaced from the support by centrifugation. The support may then contacted with the cell suspension. In this embodiment, the support may be sterile, and the procedure may be carried out under sterile conditions. The supports of the present invention can be sterilized by any methods to those of skill in the art.

Cells should be reconstituted in a volume of liquid less or equivalent to the volume removed from the support via the application of force. If the amount of cell loaded liquid added is higher than the liquid removed, the excess cell loaded liquid may not be successfully introduced into the support, which may result in a drop in seeding efficiency. The precise application of forces is desirable to partially remove the liquid from the support, without allowing it to dry. In another embodiment, the methods disclosed herein are also used to seed cells onto supports already incorporated with cells.

In another aspect, the present invention also provides a kit for seeding cells onto a support. The kit contains a support, media, and cells in media.

The Support

One of ordinary skill in the art will appreciate that the selection of a suitable material for forming the support for the device of the present invention depends on several factors. The more relevant factors in the selection of the appropriate material include bioabsorption (or biodegradation) kinetics; in vivo mechanical performance; cell response to the material in terms of cell attachment, proliferation, migration and differentiation; and biocompatibility. Other relevant factors, which to some extent dictate the in vitro and in vivo behavior of the material, include the chemical composition, spatial distribution of the constituents, the molecular weight, the degree of crystallinity, and monomer content in the case of polymeric materials. The surface properties of the materials can also be optimized to achieve the desired hydrophilicity. The methods that are used to construct the polymers used in the device of the present invention are disclosed in US patent application US20040062753 A1 and U.S. Pat. No. 4,557,264 issued Dec. 10, 1985 assigned to Ethicon, Inc.

The supports of the present invention preferably include interconnecting pores or voids, which facilitate the incorporation of cells into the support, as well as the transport of nutrients and/or expansion of cells within the support. The interconnected pores may range in size from about 50 to about 1000 microns, alternatively from about 50 to about 400 microns, and constitute about 70 to 95 percent of the total volume of the support. The range of the pore size in the support may be manipulated by modifying process steps during the preparation of the support.

Figure 2:
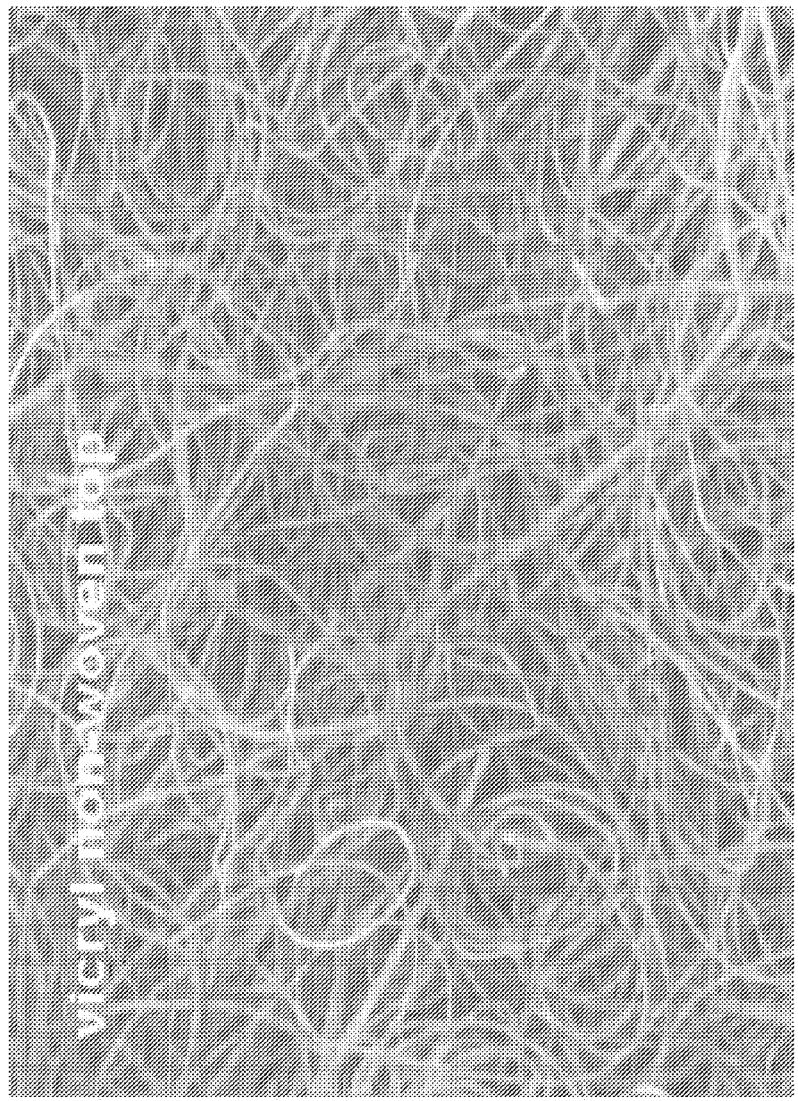
FIG. 2: Electron micrograph of a composite support of the present invention. The matrix of the support is composed of fibers made from VICRYL®. A foam component is incorporated onto the fibrous component.

Supports suitable for use in the present invention may be a highly fibrous or nonwoven support, as illustrated in FIG. 1, or a composite support, which is typically composed of a nonwoven component and a foam component as illustrated in FIG. 2. In one embodiment, the supports of the present invention have at least one pharmaceutical agent incorporated into the material forming the support.

With a composite support, the fibers encapsulated by a porous matrix may be organized in a form selected from threads, yarns, nets, laces, felts and nonwoven mats. In one embodiment, the fibers are in the form of a nonwoven fibrous mat. Known wet-lay or dry-lay fabrication techniques may be used to prepare the fibrous nonwoven mat of the composite support of the present invention ("Non-woven textiles", by Radko Krcma, Textile Trade Press, Manchester, UK, 1967).

In one aspect of the present invention, the support is a nonwoven support made from a 90/10 copolymer of PGA/PLA, sold under the trade name VICRYL® (Ethicon, Inc., Somerville, N.J.). A nonwoven VICRYL® based support is highly fibrous with a porosity range of about 70 to about 95%. In one embodiment, the nonwoven VICRYL® based support has a porosity of 90%.

In an alternate aspect, the support used in the method of the present invention is a nonwoven support made of a 95/5 copolymer of PLA/PGA, sold under the trade name PANACRYL® (Ethicon, Inc., Somerville, N.J.). A nonwoven PANACRYL® based support is highly fibrous with a porosity range of about 70 to about 95%. In one embodiment, the nonwoven PANACRYL® based support has a porosity of 90%.

In another aspect of the present invention, the support is a nonwoven support made of a 100% homopolymer of polydioxanone, sold under the trade name PDS II® (Ethicon, Inc., Somerville, N.J.). A nonwoven PDS II® based support is highly fibrous with a porosity range of about 70 to about 95%. In one embodiment, the nonwoven PDS II® based support has a porosity of 90%.

Those skilled in the art appreciate that nonwoven supports may also be prepared by mixing different ratios of the PDS II®, PANACRYL®, and VICRYL® fibers.

In an alternate aspect, the support is formed from the polymer disclosed in U.S. Pat. No. 5,686,090, European patent applications EP0878205A2, EP0325195B1 assigned to Ethicon, Inc., and European patent application EP0423155B1, assigned to Biocon OY. The polymer is sold under the tradename ETHISORB® (Ethicon Inc.).

In an alternate aspect, the present invention employs a composite support comprised of a nonwoven component and a porous foam component surrounding the fibers of the nonwoven component. The foam component may be prepared from a 65/35 PGA/PCL, 60/40 PLA/PCL, or blends thereof. A composite support for use in the present invention may have a porosity range of about 70 to about 95%. In one embodiment, the composite support has a porosity of 90%.

Alternatively, the support is a highly porous foam support, prepared from a 65/35 PGA/PCL copolymer, 60/40 PLA/PCL copolymer, or blends thereof. A foam support for use in the present invention may have a porosity range of about 70 to about 95%. In one embodiment, the foam support has a porosity of 90%.

The Cells

The cells useful for administration in this invention include autologous, allogeneic, or xenogeneic cells. In the case that the invention is intended to treat diabetes, the cells may be stem cells, pancreatic precursor/progenitor cells, genetically engineered insulin producing cells, primary or expanded partially or fully differentiated islets or insulin producing cells.

Such treatment may also be used for other types of cell therapy, including, for example, hepatocytes for the treatment of liver failure, chromaffin cells for chronic pain, cells that produce clotting factors for hemophilia, and cells that produce nerve growth factors for neurodegenerative disease such as Parkinson's or Alzheimer's disease, as well as fibroblasts, myofibroblasts, cardiovascular cells, neural cells, and neural precursor cells.

Other cells that can be therapeuticaly effective for different applications include but are not limited to progenitor cells, precursor cells, stem cells, bone marrow cells, umbilical cord blood cells, angioblasts, endothelial cells, osteoblasts, smooth muscle cells, kidney cells, fibroblasts, myofibroblasts, cardiovascular cells, neural cells, neural precursor cells, amniotic cells and postpartum placental cells. In a further embodiment of the present invention, the cells may be genetically engineered to produce a therapeutic protein, or to down-regulate the recipient's immune response.

The following examples are illustrative of the principles and practice of the invention and are not intended to limit the scope of the invention.

EXAMPLES

Example 1

Cell Seeding Onto a VICRYL® Nonwoven Support

A nonwoven biodegradable sheet approximately 2 mm in thickness was prepared from VICRYL® (90/10 PGA/PLA) fibers. Supports were then punched from the sheet using a biopsy punch with a diameter of 8 mm. Supports were then sterilized via Ethylene Oxide sterilization method. Sterile Supports were then dipped in sterile DMEM media in a sterile 50 cc Falcon tube. Once the supports were completely soaked, they were placed in a net well fitted into a 50 ml conical tube (Falcon BD). The well was then covered with a sterile tissue culture plate cover. The tube was then transferred to a centrifugation chamber (Allegra 6R).

Several centrifugation speeds (300, 400, 500, 600, 800, 1000, 1500 RPM) were applied for 5-minute periods to determine the optimum centrifugation parameters. Spinning for 5 minutes at a speed of 400-600 RPM provided enough force toremove approximately 75% of the media within the support.

This step leads to the re-creation of an appropriate space within the support without completely drying it. Spinning the support for a period of 5 minutes at a rate higher than 1000 RPM lead to a degree of dryness at which the support became too hydrophobic to allow cell incorporation.

Following centrifugation, supports were then transferred each to a separate well of a sterile 6-well tissue culture plate (Falcon BD). 1 million mesenchymal stem cells were suspended in 60 µl of media and pipetted onto each support. The cells instantaneously penetrated the support to fill the space was created via centrifugation. When a larger volume was used (approximately 100 µl), excess media flowed out of the support onto the surface of the plate carrying a significant percentage of the cells.

Following cell incorporation, supports were placed in humidified chamber, which was then placed in an incubator at 37° C. for 3 hours to allow cell attachment to the fibers of the support. Supports were then moved to new wells, each containing 10 ml of media. Remaining cells on the surface of each well were counted as follows; first three milliliters of media were added to each well and triturated up and down to collect any newly attaching cells. The media from each well was then collected and centrifuged at 1200 rpm for 5 minutes. Media was then removed and each cell pellet was re-suspended and cell number was determined using a hemocytometer. Seeding efficiency was then determined based on the total number of seeded cells and the number of cells remaining on the surface of each well. The average Seeding efficiency for five supports was approximately 95%. When a 100 µl volume was used to re-suspend the cell pellet, the seeding efficiency dropped to 60%.

Example 2

Testing Cell Viability and Distribution

Figure 3:
FIG. 3: A confocal microscope image of mesenchymal stem cells seeded into a nonwoven support. Cells were stained with a vital dye, wherein live cells stain green and dead cells stain red.

Mesenchymal stem cells (Cambrex) were seeded onto a nonwoven VICRYL® support as described in the example above. The support was then placed in DMEM with 10% FBS and incubated at 37° C. and 5% $CO_2$ for 2 days. The support was then carefully washed with PBS to remove excess media and dipped in a solution from a live-dead viability kit (molecular probes) for 10 minutes. Following that a three dimensional image was taken via a confocal microscope showing a 10 micron cross section within the support. Live cells appeared green and dead ones appeared red (FIG. 3).

Publications cited throughout this document are hereby incorporated by reference in their entirety. Although the various aspects of the invention have been illustrated above by reference to examples and preferred embodiments, it will be appreciated that the scope of the invention is defined not by the foregoing description, but by the following claims properly construed under principles of patent law.

What is claimed is:

1. A method for seeding a suspension of a plurality of cells onto a porous hydrophobic support, wherein the pores are between about 50 and about 1000 microns, comprising the steps of:
   a. Introducing a liquid media to the support,
   b. Partially removing the liquid media from the support by application of a centrifugal force, and
   c. After partially removing the liquid media, contacting the support with a suspension of a plurality of cells.

* * * * *